United States Patent
Sherman

(10) Patent No.: US 7,901,460 B2
(45) Date of Patent: *Mar. 8, 2011

(54) INTERVERTEBRAL DISC IMPLANTS AND METHODS FOR MANUFACTURING AND USING THE SAME

(75) Inventor: Michael C. Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 779 days.

This patent is subject to a terminal disclaimer.

(21) Appl. No.: 11/293,070

(22) Filed: Dec. 2, 2005

(65) Prior Publication Data

US 2006/0136064 A1 Jun. 22, 2006

Related U.S. Application Data

(63) Continuation of application No. PCT/US2004/017576, filed on Jun. 2, 2004.

(60) Provisional application No. 60/475,016, filed on Jun. 2, 2003.

(51) Int. Cl.
*A61F 2/44* (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| 3,867,728 | A | | 2/1975 | Stubstad et al. |
| 5,171,280 | A | | 12/1992 | Baumgartner |
| 5,674,192 | A | * | 10/1997 | Sahatjian et al. ............... 604/28 |
| 5,716,416 | A | * | 2/1998 | Lin ............................ 623/17.16 |
| 5,824,093 | A | * | 10/1998 | Ray et al. .................... 623/17.16 |
| 5,919,235 | A | * | 7/1999 | Husson et al. ............. 623/17.16 |
| 6,007,570 | A | | 12/1999 | Sharkey et al. |
| 6,095,149 | A | | 8/2000 | Sharkey et al. |
| 6,264,695 | B1 | * | 7/2001 | Stoy ............................ 623/17.16 |
| 6,419,694 | B1 | | 7/2002 | Sandock |
| 6,425,919 | B1 | | 7/2002 | Lambrecht |
| 6,620,196 | B1 | * | 9/2003 | Trieu ......................... 623/17.16 |
| 6,726,696 | B1 | * | 4/2004 | Houser et al. ................. 606/151 |
| 2002/0026244 | A1 | | 2/2002 | Trieu |
| 2002/0055771 | A1 | | 5/2002 | Sandock |
| 2003/0018390 | A1 | * | 1/2003 | Husson ....................... 623/17.16 |
| 2003/0100920 | A1 | * | 5/2003 | Akin et al. .................... 606/213 |
| 2005/0119750 | A1 | * | 6/2005 | Studer ......................... 623/17.16 |
| 2007/0005088 | A1 | * | 1/2007 | LeHuec et al. ................. 606/185 |

FOREIGN PATENT DOCUMENTS

| EP | 0 700 671 A1 | 3/1996 |
| WO | WO 00/59412 | 10/2000 |
| WO | WO 03/028587 A2 | 4/2003 |
| WO | WO 03/051212 A2 | 6/2003 |

* cited by examiner

*Primary Examiner* — Thomas C Barrett
*Assistant Examiner* — Nicholas Woodall

(57) ABSTRACT

Described are intervertebral disc implants that include an elastomeric polymer body, especially a hydrogel body, and a superelastic element. Also described are methods for making and using such implants.

25 Claims, 3 Drawing Sheets

US 7,901,460 B2

INTERVERTEBRAL DISC IMPLANTS AND METHODS FOR MANUFACTURING AND USING THE SAME

CROSS REFERENCE TO RELATED APPLICATIONS

The present application is a continuation of International PCT Application No. PCT/US2004/017576, filed on Jun. 2, 2004 and published on Dec. 16, 2004 as International Publication No. WO 2004/108022, which claims the benefit of U.S. Provisional Application No. 60/475,016, filed on Jun. 2, 2003, the entire contents of each application hereby being incorporated by reference.

BACKGROUND

The present invention relates generally to intervertebral disc implants, and in one particular aspect to an intervertebral disc implant having an internal core element within an elastomeric body.

As further background, a number of devices have been proposed for implantation within the spinal disc space. Many of these devices incorporate the use of an elastomeric material, for example a hydrogel. Such devices have also been proposed that can adopt a generally linear configuration for implantation through an aperture in the disc annulus, and a second, differing configuration once introduced into the disc space.

One challenge encountered in such devices is their ability to effectively transition to the desired conformation once implanted within the disc space. In addition, after taking on the desired conformation, the device must withstand the repeated loadings typically encountered in the spinal column. Aspects of the present invention address one or more of these and other needs for intervertebral disc implants.

SUMMARY

In one aspect, the present invention provides an intervertebral disc implant having a hydrogel or other similar elastomeric polymer body, and in the body an element comprised of a superelastic material. In certain forms, such implants include an elongate hydrogel body having embedded therein an elongate superelastic metal element. The superelastic element can extend along substantially the entire length of the elongate body. In one specific embodiment, an implant is provided with an elongate hydrogel body, and an elongate core element comprised of a superelastic nickel-titanium alloy. In this implant, the relaxed configuration of the hydrogel body and core element can be a spiral configuration.

In another aspect, the invention provides a method for providing an intervertebral disc implant in a patient. The method includes providing an opening in a disc annulus of the patient, and introducing through the opening and into a space defined by the disc annulus an intervertebral disc implant. The disc implant includes an elastomeric polymer body sized for introduction into the disc space and a superelastic element within the elastomeric body. In certain forms, this method includes positioning the implant to a first configuration for introduction, inserting the implant through an opening in a disc annulus and into the disc space, and allowing the implant to adopt a second configuration within the implant space differing from the first configuration.

In still another aspect, the invention provides methods of manufacturing an intervertebral disc implant. The methods include providing a superelastic element, and providing a hydrogel or other similar elastomeric body around the element. Specific embodiments of these methods involve the manufacture of intervertebral disc implants as described herein.

DESCRIPTION OF THE PREFERRED EMBODIMENTS

Figure 1:
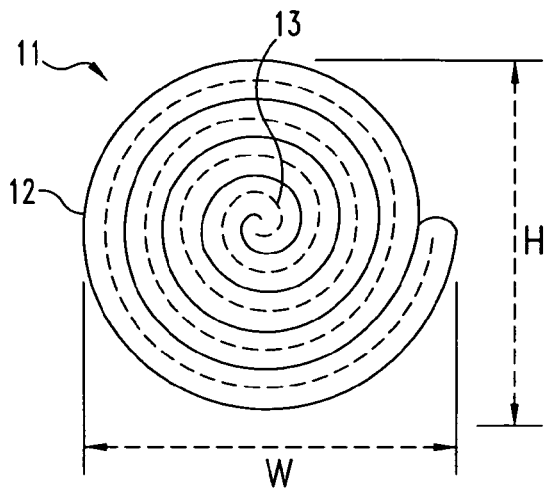
FIG. 1 provides a perspective view of one intervertebral implant of the invention.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, the present invention provides intervertebral disc implant devices and methods for their preparation and use. More specific embodiments involve spiral-form, intervertebral implants.

In certain aspects of the invention, the body of the intervertebral implant can be formed of a hydrogel or other suitable elastomeric material. Water-soluble materials can be used, so that upon implantation with the disc space, the implant increases in volume.

As to hydrogel materials suitable for use in the invention, these include lightly cross-linked biocompatible homopolymers and copolymers of hydrophilic monomers such as 2-hydroxyalkyl acrylates and methacrylates, e.g., 2-hydroxyethyl methacrylate (HEMA); N-vinyl monomers, for example, N-vinyl-2-pyrrolidone (N-VP); ethylenically unsaturated acids, for example, methacrylic acid (MA) and ethylenically unsaturated bases such as 2-(diethylamino)ethyl methacrylate (DEAEMA). The copolymers may further include residues from non-hydrophilic monomers such as alkyl methacrylates, for example, methyl methacrylate (MMA), and the like. The cross-linked polymers are formed, by known methods, in the presence of cross-linking agents, such as ethyleneglycol dimethacrylate and methylenebis(acrylamide), and initiators such as 2,2-azobis(isobutyronitrile), benzoyl peroxide, and the like, and radiation such as UV and γ-ray.

Methods for the preparation of these polymers and copolymers are well known to the art. The EWC of these hydrogels can vary, e.g., from about 38% for Polymacon™ (poly HEMA) to about 79% for Lidofilcon™ B (a copolymer of N-VP and MMA) under ambient conditions.

Another type of hydrogel, usefull in the practice of the invention, is illustrated by HYPAN™ and poly(vinyl alcohol) (PVA) hydrogels. These hydrogels, unlike the aforementioned hydrogels, are not cross-linked. Their insolubility in aqueous media is due to their partially crystalline structures. HYPAN™ is a partially hydrolyzed polyacrylonitrile. It has a multiblock copolymer (MBC) structure comprising hard crystalline nitrile blocks, which provide the hydrogel with good mechanical properties, and soft amorphous hydrophilic blocks to provide the hydrogel with good water binding capability. The methods of preparing HYPAN™ hydrogels of different water contents and mechanical properties have been disclosed in the U.S. Pat. Nos. 4,337,327, 4,370,451, 4,331,783, 4,369,294, 4,420,589, 4,379,874 and 4,631,188. The pre-nuclear forms of this material, for use in this invention, can be prepared by melt processing using solvents such as DMF and DMSO, as melting aids or by solution processing.

One particular type of hydrogel useful in the practice of this invention is highly hydrolyzed crystalline poly(vinyl alcohol) (PVA). The amount of hydrolyzation may be between 95 and 100 percent depending on the desired EWC which will be from about 60% to about 90%. Generally, the final hydrogel water content increases with decreasing hydrolyzation of the initial PVA which results in decreased crystallinity.

Partially crystalline PVA hydrogels may be prepared, from commercially available PVA powders, by any of the methods known to the art. For example, they can be prepared by the method disclosed in the U.S. Pat. No. 4,663,358, the teachings of which are incorporated herein by reference. Illustratively, 10-15% PVA powder can be mixed with a solvent, such as water, dimethyl sulfoxide (DMSO), ethylene glycol and mixtures thereof. The mixture is then heated at a temperature of about 100 to about 120° C., until a viscous solution is formed. The solution is then poured or injected into a tubular metal, glass or plastic mold and allowed to cool to below −10° C., preferably to about −20° C.

The solution is maintained at that temperature for several hours during which time crystallization and, therefore, gelation of the PVA occurs. The shaped gel is soaked with several portions of water which are periodically replaced, over a period of at least two days, until all the organic solvent in the gel has been replaced by water. The hydrated gel can then be partially or completely dehydrated for implantation. Hydrogels thus prepared can have EWC's between 60-90% and compressive strengths of at least 1 $MNm^{-2}$, preferably about 4 $MNm^{-2}$, when subject to the same constraints as the natural nucleus in an intervertebral disc.

Completion of the solvent exchange can be determined by known methods. For instance, when the solvent is DMSO its removal from the gel, is determined as follows: 50 µL of a 0.01 N $KMnO_4$ solution are added to 50 mL aliquots of the water which has been separated from the gels. The presence of DMSO in the water will be indicated by disappearance of the characteristic pink color of the $KMnO_4$. When the DMSO has been completely removed the pink color will not disappear. This method has a detection limit of 0.3 ppm, for DMSO, when compared to a blank and 0.3 ppm aqueous DMSO standard.

In general, any hydrogel that can be used for biomedical purposes can be used. In certain forms of the invention, the hydrogel will exhibit an EWC from about 30 to about 90% and a compressive strength of at least about 1 $MNm^{-2}$, preferably 4 $MNm^{-2}$, when subjected to the constraints of the annulus and end plates of the disc. Shaped implants from these materials, e.g., a rod or tube, in a dehydrated form (xerogels), can be prepared either by cast molding or lathe cutting. In cast molding, the liquid monomer mixture, with initiator, is poured into a mold of predetermined shape and size, and cured. If desired, the casting mixture may include water, or another aqueous medium. Under those circumstances the resultant shaped article will be partially hydrated, i.e., a hydrogel. In the case of lathe cutting, the xerogel can be prepared, in a similar manner to the above, in the form of a block or rod which is larger than needed to form the prosthetic nucleus. The xerogel is then cut to the shape and size required for implantation into the disc cavity. In both cases, the hydrogel expansion factor, due to polymer swelling upon hydration, has to be taken into account in designing the mold or in cutting the block, rod or tube.

Certain embodiments in the invention provide implants that incorporate an internal or core element comprised of a superelastic material. In one illustrative example, such implants can be prepared by molding or casting the elastomeric (e.g. hydrogel) polymer body around the superelastic element.

Superelastic materials are known to exhibit unusual elasticity and flexibility. These materials also typically exhibit a shape memory effect. When plastically deformed from an original shape at one temperature, the materials will recover their original shape on being raised to a higher temperature.

Superelastic materials are known to undergo a transformation known as martensitic transformation, wherein they change from a high temperature form called austenite, to a low temperature form called martinsite. For a given superelastic alloy, the transformation between martinsite and austenite forms occurs at a predictable temperature, known as the transformation temperature.

As to these temperature dependent properties, to exhibit a shape memory effect, constructs of superelastic alloys must first be bent into a shape to be "memorized" at room temperature. The alloy element is then heated until it assumes a high temperature configuration called the beta or parent phase. In this phase, the crystal structure of the metal assumes its austenite form which it will "remember". Afterwards, the alloy is rapidly cooled such that the atoms in the alloy rearrange themselves into the crystal form of martinsite. The alloy can then be bent into a new shape which it will maintain as long as the temperature remains below the transformation temperature. Subsequent heating of the element above its transformation temperature so that the alloy structure reverts to an austenite form will cause the element to recover its previously memorized shape.

Intervertebral implants of the invention can be manufactured so as to utilize these shape memory properties of superelastic materials. For instance, shape memory properties of the superelastic element can facilitate the transition of an intervertebral disc implant from a first configuration during introduction, to a second configuration after introduction and upon reaching the body temperature of the patient. Alternatively or in addition, these temperature dependent shape memory properties can provide a residual force within the implant in its second, implanted configuration, to stabilize the implant in that configuration.

Illustratively, a superelastic material with a transformation temperature between a relatively lower temperature at which the implant will be introduced and a higher temperature of the patient's body can be used. A superelastic element (e.g., an elongate wire or similar element) can be shaped to the second, implanted configuration (e.g., a spiral), and heated until its the crystal structure assumes its austenite, "memorized" form. After cooling to form the martinsite crystal form, the superelastic element can be bent to straighten it, and then the elastomeric body provided around the superelastic element, such as by molding or casting a hydrogel body around the element. Thereafter, upon introduction, the superelastic element will be heated by the patient's body heat to a temperature above its transformation temperature, and thus revert to its second, implanted configuration. It will be understood in this regard that such shape memory effects can also be used in conjunction with the superelastic, temperature-independent properties to facilitate transition between the first and second configurations.

In another illustrative embodiment using a superelastic material having an intermediate transformation temperature as described above, the superelastic element can be used to further stabilize the implant in its second, implanted configuration. For instance, for implanted configurations, such as spiraled or folded shapes, wherein two portions of the implant will contact one another, the shape memory properties of the superelastic element can be used to forcibly maintain that contact and thus stabilize the final configuration.

In a specific exemplary embodiment, an elongate superelastic element can be formed to a spiral somewhat tighter or more acute than that to be found in the final, implanted configuration, and then heated to introduce memory of that form, and cooled. The spiral element can then be bent to a less acute form approximating that desired in the implanted configuration, and then an elongate hydrogel body provided (e.g., molded or cast) around and following the spiral element. For introduction, the spiral-form implant can be forcibly straightened. Upon introduction, the implant will relax to its implanted configuration with portions contacting one another, and then the superelastic element will be heated by the patient's body heat to a temperature above its transformation temperature, thus providing a residual, lasting force to maintain the contact points in the implant.

As noted above, superelastic materials also have useful temperature independent properties. Superelastic alloys exhibit significantly increased resiliency relative to non-superelastic materials, because the atoms of the memory metal shift back and forth between martinsite and austenite forms, and do not slip into new dislocated configurations as is the case with normal metals. In an alloy that has a beta phase capable of producing martinsite under stress, an unusual elastic property called superelasticity is observed. Typically alloys with this property exhibit normal elastic behavior under stress until a critical stress is reached, at which point martinsite molecular structures begin to form. With further stress, the element continues to elongate as if it were being physically deformed. Upon removal of the stress, the martinsite structure reverts to the parent phase, or austenite structure, and the metal contracts to its original dimensions, showing substantially no permanent deformation.

In a specific embodiment, the superelastic material can be a nickel-titanium alloy such as that commercially available as Nitinol.

With reference now to FIG. 1, shown is a perspective view of one intervertebral disc implant of the present invention. Implant 11 includes elastomeric body 12 made of a polymeric material, particularly hydrogel. Embedded within body 12 is a core element 13 made of a superelastic material, such as a superelastic nickel-titanium alloy. Implant 11 has a height H and a width W suitable for implantation within the disc space defined by a disc annulus.

Figure 2:
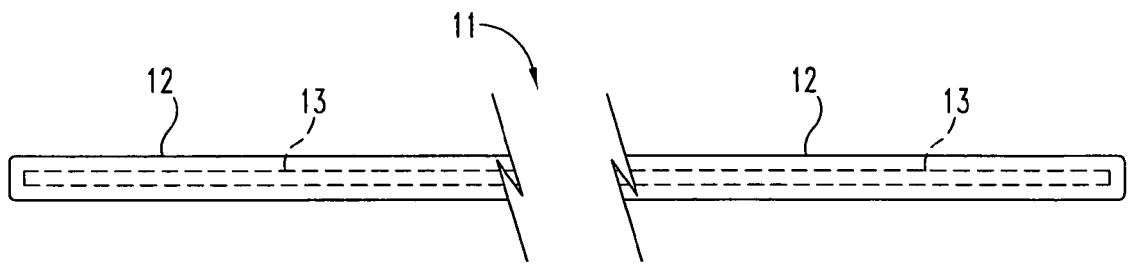
FIG. 2 provides a perspective view of the implant of FIG. 1 in a straightened configuration.

With reference now to FIG. 2, shown is implant 11 of FIG. 1 in a linear or straightened configuration. As shown, both elastomeric body 12 and superelastic core element 13 are in a relatively linear configuration, rendering the device to a convenient state for passage through a cannula and into the disc space.

Figure 3A:
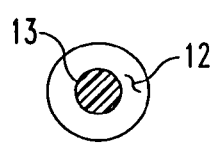
FIGS. 3A and 3B provide cross-sectional views of the implant of FIGS. 1 and 2 in a relatively non swelled, and swelled state, respectively.
Figure 3B:
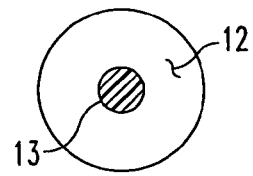
Figure 4:
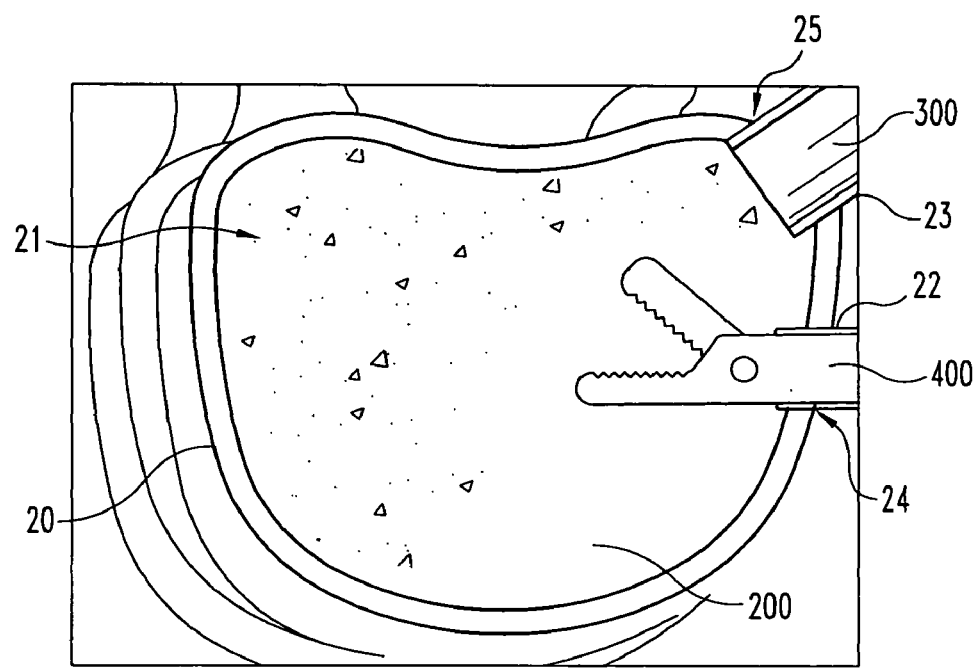
FIGS. 4-6 provide illustrations of steps that can be taken during introduction of intervertebral implants of the invention.

With reference to FIGS. 3A and 3B, shown are cross-sectional views of the device of FIG. 2. In FIG. 3, implant body 12 is formed of a hydrogel which is dehydrated or only partially hydrated, therefore having a relatively smaller cross-sectional dimension. Shown in FIG. 4 is the same implant body 12 having a more or completely hydrated form and thus a larger cross-sectional dimension. As will be understood, the implant in the completely or partially dehydrated state as shown in FIG. 3 will be more readily passed through a smaller cannula and smaller opening in the disc annulus, for delivery to the disc space. Thereafter, implant 11 will take up water and swell to a larger dimension.

Figure 5:
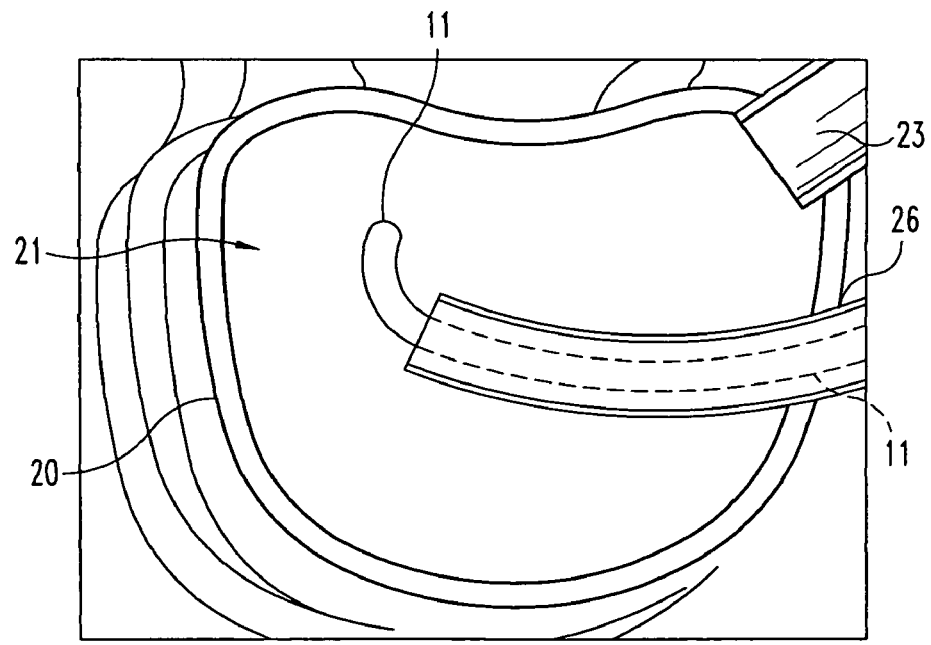
Figure 6:
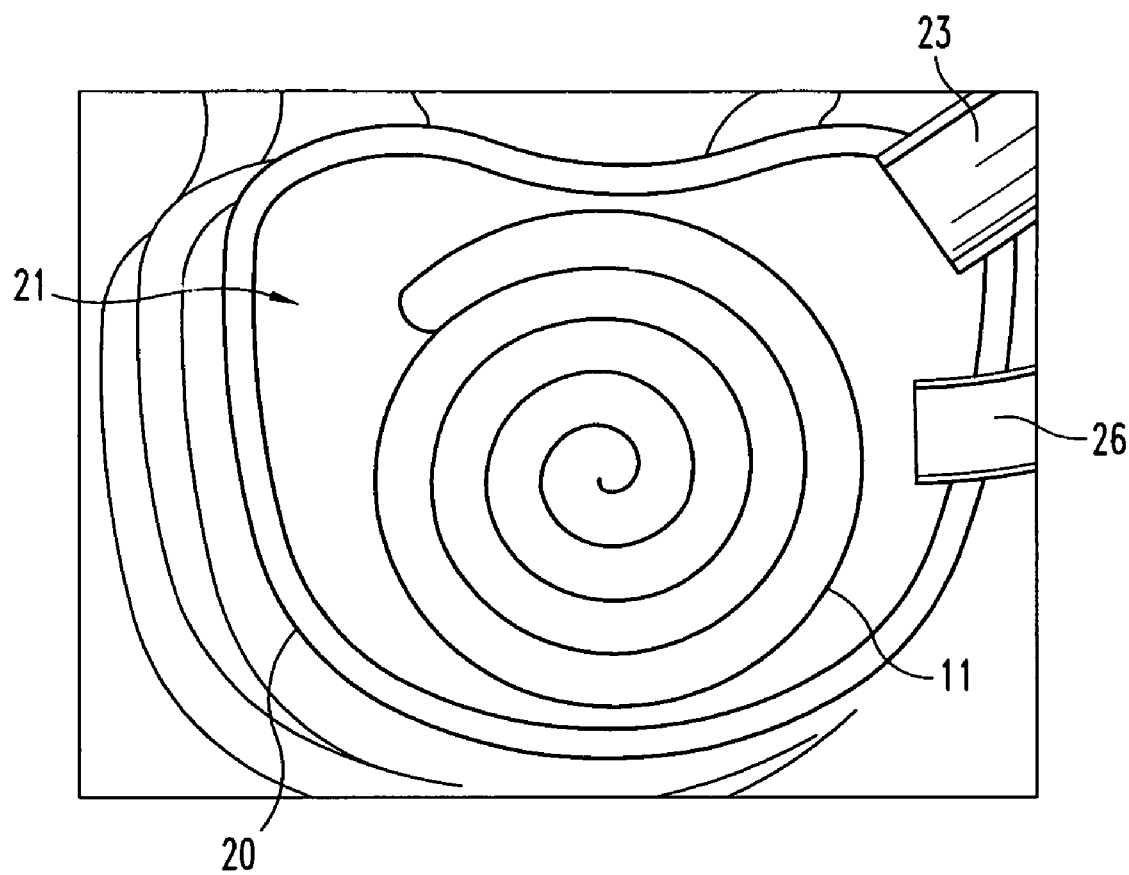

With reference to FIGS. 4-6, generally shown are steps to be taken in one procedure of the invention. In a first step, the disc annulus 20 is provided with one or more openings into the interior disc space 21. These openings can be provided, for example, by a cutting or dissecting instrument such as a scalpel. In addition, it will be understood that an access cannula, such as a tissue retraction cannula, and be provided extending to the one or more openings, through which other surgical instruments as discussed herein can be manipulated.

A tissue disrupting instrument 22 is used to disrupt nucleus tissue from within the disc space 21, which tissue can optionally be withdrawn under vacuum. An endoscope 23 or other visualization device extending through opening 25 in disc annulus 20 can be used to visualize the disc space. Referring to FIG. 5, after any removal of material desired from the disc space 21, an introducer cannula 26 is inserted through opening 24, and implant 11 is passed through cannula 26 and delivered into the disc space 21. Referring now to FIG. 6, shown is implant 11 having taken on its implanted configuration in a generally coiled or spiral shape. After introduction of the implant 11, delivery cannula 26 can be withdrawn, and endoscope 23 can also be withdrawn, along with any access cannula(s) utilized in the surgery. If desired, openings 24 and 25 in annulus 20 can be patched or sealed with suitable materials therefore.

In one embodiment of the invention, implant 11 is provided in a kit or system along with at least one other device for use in the disc surgery, for example, delivery cannula 26, visualization device 23, tissue disruption device 22, access cannula(s), etc. Any combination of some or all of these and/or other devices along with implant 11 can be incorporated into a surgical kit or system in accordance with the invention.

Further, implants of the invention can have one or more implant bodies having any of a wide variety of shapes or configurations. As several specific illustrations, superelastic core elements, e.g., corresponding to core element 13 disclosed herein, can be incorporated into the implant bodies and shapes disclosed in U.S. Pat. No. 6,620,196 issued Sep. 16, 2003 and assigned to SDGI Holdings Inc., and can be adapted to facilitate transition of the implants to an intended implanted configuration and/or stabilize the implants in such configuration.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are indicative of the abilities of those of ordinary skill in the art and are hereby incorporated by reference in their entirety as if individually incorporated by reference and fully set forth.

What is claimed is:

1. An intervertebral disc implant, comprising:
    an elastomeric polymer body sized for introduction into a disc space; and
    a superelastic element within the elastomeric body, the superelastic element comprising a superelastic metal alloy having shape-memory properties; and
    wherein each of said elastomeric polymer body and said superelastic element are elongate and each have a generally linear and substantially straight insertion configuration that is transitioned to an implanted configuration upon introduction into the disc space, said implanted configuration comprising a coiled configuration having a spiral shape; and wherein said coiled configuration includes multiple coils spiraling about a center of the implant, and wherein a central region of the implant in said coiled configuration is substantially solid; and wherein said shape-memory properties of said superelastic element forcibly maintains adjacent ones of said multiple coils in contact with one another by a residual force to thereby stabilize said coiled configuration of the implant.

2. The intervertebral disc implant of claim 1, wherein the elastomeric polymer body is water-swellable.

3. The intervertebral disc implant of claim 2, wherein the elastomeric polymer body comprises a hydrogel.

4. The intervertebral disc implant of claim 1, wherein said elastomeric polymer body comprises a water-swellable material that is dehydrated or partially hydrated when the implant is in said insertion configuration, said elastomeric polymer body having a first volume when the implant is in said insertion configuration; and wherein said water-swellable material has increased hydration when the implant is transitioned to said implanted configuration within the disc space, said elastomeric polymer body having a second volume in said implanted configuration that is larger than said first volume in said insertion configuration.

5. The intervertebral disc implant of claim 1, wherein said coiled configuration includes at least three of said coils that each spiral a full 360 degrees about said center of the implant.

6. The intervertebral disc implant of claim 5, wherein said coiled configuration includes four of said coils that each spiral a full 360 degrees about said center of the implant.

7. An intervertebral disc implant, comprising:
an outer element formed of an elastomeric material; and
an inner core element formed of a shape-memory material comprising a superelastic metal alloy having shape-memory properties, said inner core element embedded within said elastomeric material of said outer element; and wherein the implant has an insertion configuration sized and shaped for introduction into an intervertebral disc space with each of said outer element and said inner core element having a generally linear and substantially straight configuration when said implant is in said insertion configuration; and wherein the implant is transitioned from said insertion configuration to a different implanted configuration upon introduction into the intervertebral disc space, said implanted configuration comprising a coiled configuration having a spiral shape; and wherein said coiled configuration includes multiple coils spiraling about a center of the implant, and wherein a central region of the implant in said coiled configuration is substantially solid; and wherein said shape-memory properties of said inner core element forcibly maintains adjacent ones of said multiple coils in contact with one another by a residual force to thereby stabilize said coiled configuration of the implant.

8. The intervertebral disc implant of claim 7, wherein said elastomeric material comprises a water-swellable material that is dehydrated or partially hydrated when the implant is in said insertion configuration, said outer element having a first cross-sectional dimension when the implant is in said insertion configuration; and wherein said water-swellable material has increased hydration when the implant is transitioned to said implanted configuration within the intervertebral disc space, said outer element having a second cross-sectional dimension in said implanted configuration that is larger than said first cross-sectional dimension in said insertion configuration.

9. The intervertebral disc implant of claim 8, wherein said water-swellable material comprises a hydrogel material.

10. The intervertebral disc implant of claim 7, wherein said elastomeric material comprises a polymeric material.

11. The intervertebral disc implant of claim 10, wherein said polymeric material comprises a hydrogel material.

12. The intervertebral disc implant of claim 7, wherein said shape-memory material exhibits superelastic characteristics; and wherein the implant is transitioned from an initial configuration to said insertion configuration upon imposition of stress onto the implant; and wherein the implant is automatically transitioned from said insertion configuration to said implanted configuration without a corresponding change in temperature upon removal of said stress on the implant.

13. The intervertebral disc implant of claim 12, wherein said initial configuration comprises a first coiled configuration; and wherein the implant is transitioned from said first coiled configuration to a generally linear and substantially straight configuration defining said insertion configuration upon imposition of said stress onto the implant; and wherein the implant is transitioned from said generally linear and substantially straight configuration to a second coiled configuration defining said implanted configuration upon removal of said stress on the implant.

14. The intervertebral disc implant of claim 7, wherein said shape-memory material is transitioned from said insertion configuration to said implanted configuration in response to a corresponding change in temperature upon insertion into the intervertebral disc space.

15. The intervertebral disc implant of claim 7, wherein said elastomeric material comprises a water-swellable material that is dehydrated or partially hydrated when the implant is in said insertion configuration, said outer element having a first volume when the implant is in said insertion configuration; and wherein said water-swellable material has increased hydration when the implant is transitioned to said implanted configuration within the intervertebral disc space, said outer element having a second volume in said implanted configuration that is larger than said first volume in said insertion configuration.

16. The intervertebral disc implant of claim 7, wherein said coiled configuration includes at least three of said coils that each spiral a full 360 degrees about said center of the implant.

17. The intervertebral disc implant of claim 16, wherein said coiled configuration includes four of said coils that each spiral a full 360 degrees about said center of the implant.

18. An intervertebral disc implant, comprising:
an outer element formed of an elastomeric hydrogel material; and
an inner core element formed of a shape-memory material having shape-memory properties, said inner core element embedded within said elastomeric hydrogel material of said outer element; and wherein the implant has an insertion configuration sized and shaped for introduction into an intervertebral disc space, said elastomeric hydrogel material being dehydrated or partially hydrated when the implant is in said insertion configuration to provide said outer element with a first cross-sectional dimension;

wherein the implant is transitioned from said insertion configuration to a different implanted configuration upon introduction into the intervertebral disc space, said elastomeric hydrogel material having increased hydration when the implant is transitioned to said implanted configuration within the intervertebral disc space to provide said outer element with a second cross-sectional dimension larger than said first cross-sectional dimension; and wherein said insertion configuration comprises a generally linear and substantially straight configuration with each of said outer element and said inner core element being generally linear and substantially straight when said implant is in said insertion configuration; and wherein said implanted configuration comprises a coiled configuration with each of said outer element and said inner core element having a spiral shape when said implant is in said coiled configuration; and wherein said coiled configuration includes multiple coils spiraling about a center of the implant, and wherein a central region of the implant in said coiled configuration is substantially solid; and wherein said shape-memory properties of said inner core element forcibly maintains adjacent ones of said multiple coils in contact with one another by a residual force to thereby stabilize said coiled configuration of the implant.

19. The intervertebral disc implant of claim 18, wherein said shape-memory material exhibits superelastic characteristics; and wherein the implant is transitioned from an initial configuration to said insertion configuration upon imposition of stress onto the implant; and wherein the implant is automatically transitioned from said insertion configuration to said implanted configuration upon removal of said stress on the implant.

20. The intervertebral disc implant of claim 19, wherein said initial configuration comprises a first coiled configuration; and wherein the implant is transitioned from said first coiled configuration to said generally linear and substantially straight configuration defining said insertion configuration upon imposition of said stress onto the implant; and wherein the implant is transitioned from said generally linear and substantially straight configuration to a second coiled configuration defining said implanted configuration upon removal of said stress on the implant.

21. The intervertebral disc implant of claim 18, wherein said shape-memory material is transitioned from said insertion configuration to said implanted configuration in response to a corresponding change in temperature upon insertion into the intervertebral disc space; and wherein said substantially straight configuration is transitioned to said coiled configuration defining said implanted configuration upon said corresponding change in temperature.

22. The intervertebral disc implant of claim 18, wherein said coiled configuration includes at least three of said coils that each spiral a full 360 degrees about said center of the implant.

23. The intervertebral disc implant of claim 22, wherein said coiled configuration includes four of said coils that each spiral a full 360 degrees about said center of the implant.

24. An intervertebral disc implant, comprising:

an outer element formed of an elastomeric hydrogel material; and an inner core element formed of a shape-memory material, said inner core element embedded within said elastomeric hydrogel material of said outer element; and wherein the implant has an insertion configuration sized and shaped for introduction into an intervertebral disc space. said elastomeric hydrogel material being dehydrated or partially hydrated when the implant is in said insertion configuration to provide said outer element with a first cross-sectional dimension;

wherein the implant is transitioned from said insertion configuration to a different implanted configuration upon introduction into the intervertebral disc space, said elastomeric hydrogel material having increased hydration when the implant is transitioned to said implanted configuration within the intervertebral disc space to provide said outer element with a second cross-sectional dimension larger than said first cross-sectional dimension; and wherein said insertion configuration comprises a generally linear and substantially straight configuration with each of said outer element and said inner core element being generally linear and substantially straight when said implant is in said insertion configuration; and wherein said implanted configuration comprises a coiled configuration with each of said outer element and said inner core element having a spiral shape when said implant is in said coiled configuration; and wherein said coiled configuration includes multiple coils spiraling about a center of the implant, and wherein a central region of the implant in said coiled configuration is substantially solid; and wherein said outer element has a first volume when the implant is in said insertion configuration, said outer element having a second volume in said implanted configuration that is larger than said first volume.

25. The intervertebral disc implant of claim 24, wherein said shape-memory material has shape-memory properties; and wherein said shape-memory properties of said inner core element forcibly maintains adjacent ones of said multiple coils in contact with one another by a residual force to thereby stabilize said coiled configuration of the implant.

* * * * *